US00PP10075P

United States Patent [19]

Challet

[11] Patent Number: Plant 10,075

[45] Date of Patent: Oct. 21, 1997

[54] CHRYSANTHEMUM PLANT NAMED 'CHALOTARI'

[75] Inventor: Jean Pierre Challet, Nuaille, France

[73] Assignee: Selection New Plant SARL, Le Luc, France

[21] Appl. No.: 710,152

[22] Filed: Sep. 12, 1996

[51] Int. Cl.[6] ..... A01H 5/00

[52] U.S. Cl. ..... Plt./76

[58] Field of Search ..... Plt./76, 80, 81

*Primary Examiner*—Howard J. Locker

*Attorney, Agent, or Firm*—Burns, Doane, Swecker & Mathis, L.L.P.

[57] ABSTRACT

A new and distinct Chrysanthemum cultivar named 'Chalotari' is provided. The new cultivar was the result of a controlled breeding program. Attractive very large double incurved blossoms of the pompon type are formed that display an attractive light pink coloration when viewed from a distance. The blossoms assume the configuration of a round ball. The incurving is particularly pronounced at the tips of the ray florets; however, ray florets present in the outer rows may be somewhat reflexed. The blossoms are long lasting and keep their form for approximately three weeks. The response period of the flowers is approximately ten weeks. Recurrent profuse flower production throughout the year is possible. The plant possesses strong stems, forms large dark green glossy leaves, and commonly assumes a height of approximately 45 to 50 cm. The blossom coloration contrasts nicely with the dark green foliage. The new cultivar is particularly suited for use in the production of a decorative pot Chrysanthemum that grows well single stem or disbudded. No growth regulator is necessary to achieve the short to medium plant height.

1 Drawing Sheet

SUMMARY OF THE INVENTION

The present invention comprises a new and distinct cultivar of Chrysanthemum, botanically known as *Dendranthema grandiflora*, and hereinafter is referred to by the cultivar name 'Chalotari'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during November 1989 at Nuaille, Trementines, France. The female parent (i.e., the seed parent) was the 'Chaloca' cultivar (non-patented in the United States) having large pink flowers, weak stems, a response time of nine weeks, and a medium to tall plant height, and the male parent (i.e., the pollen parent) was a plant designated '8759-4' (non-patented in the United States and has never has commercialized) having large white flowers, and a very attractive foliage. The 'Chaloca' parent is being marketed under the OCARINA trademark. The parentage of the new cultivar can be summarized as follows:

'Chaloca'×'8759-4'.

The seeds resulting from the above pollination were sown and many small plantlets were obtained which were physically and biologically different from each other. Selective study resulted in the identification of a single plant of the new variety.

It was found that the new cultivar of the present invention:

(a) exhibits attractive large double incurved pompon blossoms that are purple on the inner surfaces and much paler on the outer surfaces, and convey a light pink tonality when viewed from a distance, (b) exhibits a flower response period of approximately ten weeks, (c) forms attractive dark green foliage, (d) achieves a short to medium plant height, and (e) is particularly suited for pot mum production on a recurrent basis throughout the year.

The new cultivar is intended primarily as a decorative pot Chrysanthemum for growing indoors. However, it also can be grown for cut flower production in those instances where stems of approximately 50 cm. or less are acceptable. Also, the new cultivar can be grown outdoors at temperatures above freezing.

In the absence of debudding the new cultivar commonly forms approximately 9 to 13 blossoms per stem. The new cultivar can be grown single stem or disbudded. An increased number of branches readily can be induced by pinching. The pinching of a cutting commonly produces approximately 3 stems per cutting. No growth regulator is required to produce the short to medium plant height; however, a growth regulator optionally can be utilized.

The new cultivar can be considered to be an October-flowering greenhouse variety with the natural flowering season commonly occurring in weeks 42 and 43 of the year. Attractive blossoms can be produced on a recurrent basis throughout the year with the indicated ten week response period. The blossoms are long lasting and commonly can be maintained on the plant for approximately three weeks.

Asexual reproduction of the new cultivar by cuttings initially taken during 1990, as performed in Nuaille, Trementines, France, in a controlled environment has demonstrated that the characteristics of the new cultivar as herein described are firmly fixed and are retained through successive generations of asexual propagation.

'Chalotari' has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the 'Chalecat' cultivar (U.S. Plant Pat. No. 9,463), the 'Chalotari' cultivar is found to exhibit a different flower color, a longer stem, and a somewhat more double flower.

The new 'Chalotari' cultivar is being marketed under the AIDA trademark.

BRIEF DESCRIPTION OF THE PHOTOGRAPH

The accompanying photograph was prepared during arch, 1996, and shows as nearly true as it is reasonably ssible to make the same in a color illustration of this aracter, typical plants and plant parts of the new cultivar the present invention. The plants were twelve weeks of e and were grown at Nuaille, Trementines, France, under andard greenhouse conditions which approximate those mmonly utilized for the production of decorative pot ums. The plant had been disbudded except where indicated order to encourage the formation of one large bloom per em.

DETAILED DESCRIPTION

Figures 1, 2, 3, 4, 5, 6, 7, 8, 9, 10, 11, 12, 13, 14, 15:
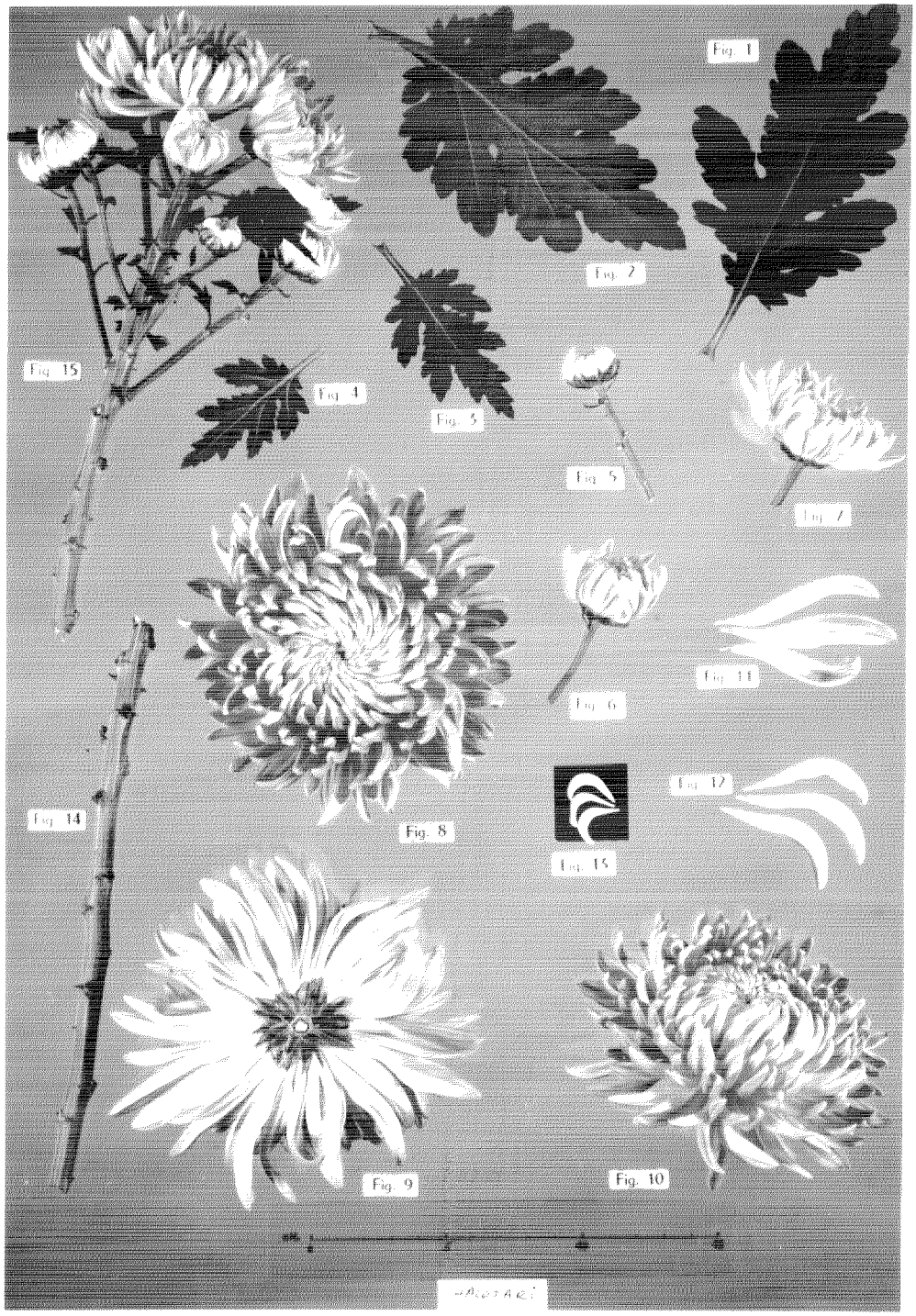
FIG. 1 illustrates the upper leaf surface of a typical leaf om the lower part of the stem.
FIG. 2 illustrates the under leaf surface of a typical leaf om the lower part of the stem.
FIG. 3 illustrates the upper leaf surface of a typical leaf om the upper part of the stem.
FIG. 4 illustrates the under leaf surface of a typical leaf rom the upper part of the stem.
FIG. 5 illustrates the side view of an unopened bud.
FIG. 6 illustrates the side view of a bud during the course of opening.
FIG. 7 illustrates the side view of a flower during the course of opening with a few outer florets being fully expanded.
FIG. 8 illustrates an obverse view of a fully expanded flower.
FIG. 9 illustrates a reverse view of a fully expanded flower.
FIG. 10 illustrates a perspective view of a fully expanded flower.
FIG. 11 illustrates an obverse view of three typical outer ray-florets.
FIG. 12 illustrates a reverse view of three typical outer ray-florets.
FIG. 13 illustrates an obverse view of three typical inner ray-florets.
FIG. 14 illustrates a typical stem.
FIG. 15 illustrates a side of a typical inflorescence wherein no disbudding was practiced.

The chart used in the identification of colors described hereafter is The R.H.S. Colour Chart of The Royal Horticultural Society, London, England. In some instances more common color terms are provided and are to be accorded their usual dictionary significance. The plants described were grown at Nuaille, Trementines, France, in 20 cm. pots, three plants to a pot, were rooted in early June, and were stopped in mid-July. All primary laterals were retained, disbudding was carried out to leave the terminal flower heads, the plants were grown outdoors until late September, and then were grown in greenhouses provided at a mimimum temperature of 15.5° C. These conditions were deemed to approximate those commonly utilized for the production of decorative pot mums.

Classification:

*Botanical.*—*Dendranthema grandiflora*, cv. 'Chalotari'.

*Commercial.*—Decorative pot mum.

Inflorescence

A. Capitulum:

*Form.*—Large, double, incurved, and commonly exhibiting a reflexed outer row of ray florets.

*Type.*—Pompon.

*Diameter across face.*—Approximately 13 to 15 cm. on average when fully expanded.

B. Corolla of ray and disc florets:

*Disc florets.*—Tubular, few in number, very difficult to observe, and tend to be scattered among the ray florets with a small cluster at the apex of the receptacle that is visible only when the ray florets are removed.

*General tonality.*—Light pastel pink due to the pale coloration of the outer surfaces of the tips of the outer ray florets.

*Color ray florets.*—When the flowers are fully expanded, the outer surfaces of most florets of the outer row are Purple Group 75B but lack a solid color presentation, and tend to become paler towards the tips. When the flowers are fully expanded, the inner surfaces of most florets of the outer row are Red-Purple Group 72B presented in streaks and patches over white, giving an impression of near Purple-Violet Group 80C. When the outer row of florets is fully expanded, the outer surfaces of the inner florets are near Purple Group 75C, but are considerably paler. Also, the coloration is not as a solid presentation and becomes more yellow towards the base. When the outer row of florets is fully expanded, the inner surfaces of the inner florets are White Group 155D overlaid with Red-Purple Group 72B in streaks and patches on the distal half, and generally provide an impression of Purple-Violet Group 80C but is considerably paler.

*Configuration ray petals.*—The longitudinal axis of most petals is incurving with a medium to strong degree of curvation along the distal half. The longitudinal axis of the outer row is reflexed to a medium degree along most of the axis. The cross section of ray florets is concave. The length of the corolla tube is very short, and occasionally is short. The thickness of the ray florets is medium, and their surfaces are textured. The tips of the ray florets are dentated, and occasionally are mamillate. The ray florets commonly are approximately 72 mm. in length and approximately 13 mm. in width on average.

C. Reproductive organs:

*Androecium.*—Generally present with disc florets and absent in ray florets.

*Gynoecium.*—Generally present with most disc florets and with most ray florets.

*Pollen.*—Formed in a slight quantity and golden-yellow in coloration.

*Fragrance.*—Typical of Chrysanthemum.

Plant

A. General appearance:

*Height.*—Short to medium, and approximately 45 to 50 cm. in height on average.

B. Foliage

*Color.*—Green Group 137C.

*Configuration.*—Lobed (as illustrated).

*Texture.*—Fleshy.

*Serration.*—Medium to coarse.

*Length of lower lobe.*—Medium to long, and occasionally are longer.

*Shape of base.*—Cordate.

*Claw in base of sinus between lateral lobes.*—Present.

*Margins of sinus between lateral lobes.*—Converging.

*Apex.*—Mucronate.

*Stems.*—Strong, annular in cross-section, nearest to Yellow-Green Group 146B in coloration, and mainly with anthocyanin coloration at the nodes.

I claim:

1. A new and distinct cultivar of Chrysanthemum plant named 'Chalotari', substantially as herein shown and described, which:

(a) exhibits attractive large double incurved pompon blossoms that are purple on the inner surfaces and much paler on the outer surfaces and convey a light pink tonality when viewed from a distance, (b) exhibits a flower response period of approximately ten weeks, (c) forms attractive dark green foliage, (d) achieves a short to medium plant height, and (e) is particularly suited for pot mum production on a recurrent basis throughout the year.

* * * * *